United States Patent
Espinal

(10) Patent No.: US 8,449,569 B2
(45) Date of Patent: May 28, 2013

(54) APPARATUS FOR MANIPULATION OF IMPLANTABLE MEDICAL DEVICE AND ASSOCIATED METHOD

(75) Inventor: Eric A. Espinal, Akron, OH (US)

(73) Assignee: Mit Capital Partners, LLC, Akron, OH (US)

( * ) Notice: Subject to any disclaimer, the term of this patent is extended or adjusted under 35 U.S.C. 154(b) by 583 days.

(21) Appl. No.: 12/649,786

(22) Filed: Dec. 30, 2009

(65) Prior Publication Data

US 2011/0160743 A1    Jun. 30, 2011

(51) Int. Cl.
*A61B 17/00* (2006.01)
*A61B 19/00* (2006.01)

(52) U.S. Cl.
USPC .......................................... 606/205; 606/129

(58) Field of Classification Search
USPC ........... 606/129, 205–208, 130; 607/128–131
See application file for complete search history.

(56) References Cited

U.S. PATENT DOCUMENTS

| | | | |
|---|---|---|---|
| 3,737,579 A | 6/1973 | Bolduc | |
| 4,207,903 A | 6/1980 | O'Neill | |
| 4,271,846 A | 6/1981 | Little | |
| 5,139,033 A | 8/1992 | Everett et al. | |
| 5,466,243 A * | 11/1995 | Schmieding et al. | 606/232 |
| 5,893,835 A * | 4/1999 | Witt et al. | 601/2 |
| 5,951,575 A * | 9/1999 | Bolduc et al. | 606/144 |
| 7,251,532 B2 | 7/2007 | Hess et al. | |
| 7,270,669 B1 | 9/2007 | Sra | |
| 2005/0004644 A1 * | 1/2005 | Kelsch et al. | 607/131 |
| 2008/0255608 A1 * | 10/2008 | Hinman et al. | 606/205 |

OTHER PUBLICATIONS

Herrmann et al., Cell-Based Therapy for Ischemic Heart Disease: A Clinical Update, The Annals of Thoracic Surgery, The Society of Thoracic Surgeons, vol. 88, No. 5, Nov. 2009, pp. 1714-1722.

* cited by examiner

*Primary Examiner* — Katherine Dowe
(74) *Attorney, Agent, or Firm* — Fay Sharpe LLP

(57) ABSTRACT

A surgical device for manipulation of an implantable medical device includes a surgical tool and a controller. The surgical tool may include a mechanical interface that enables a surgical instrument to hold and position the surgical tool, an electrical drive mechanism with a drive shaft, the electrical drive mechanism selectively controlling bidirectional rotation of the drive shaft, and a grasping mechanism operationally coupled to the drive shaft. The grasping mechanism for releasably grasping the implantable medical device. The controller includes a first control device. An implant activation of the first control device controls the electrical drive mechanism to rotate the grasping mechanism in a first direction. A removal activation of the first control device controls the electrical drive mechanism to rotate the grasping mechanism in an opposite direction. A method for manipulation of the implantable medical device is also provided.

22 Claims, 9 Drawing Sheets

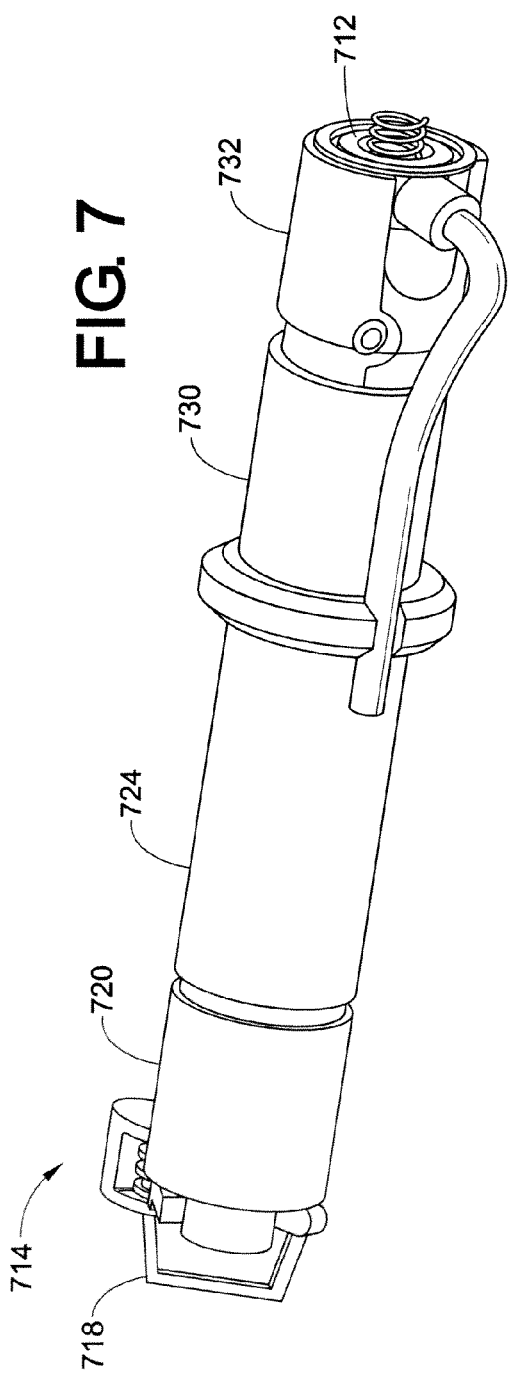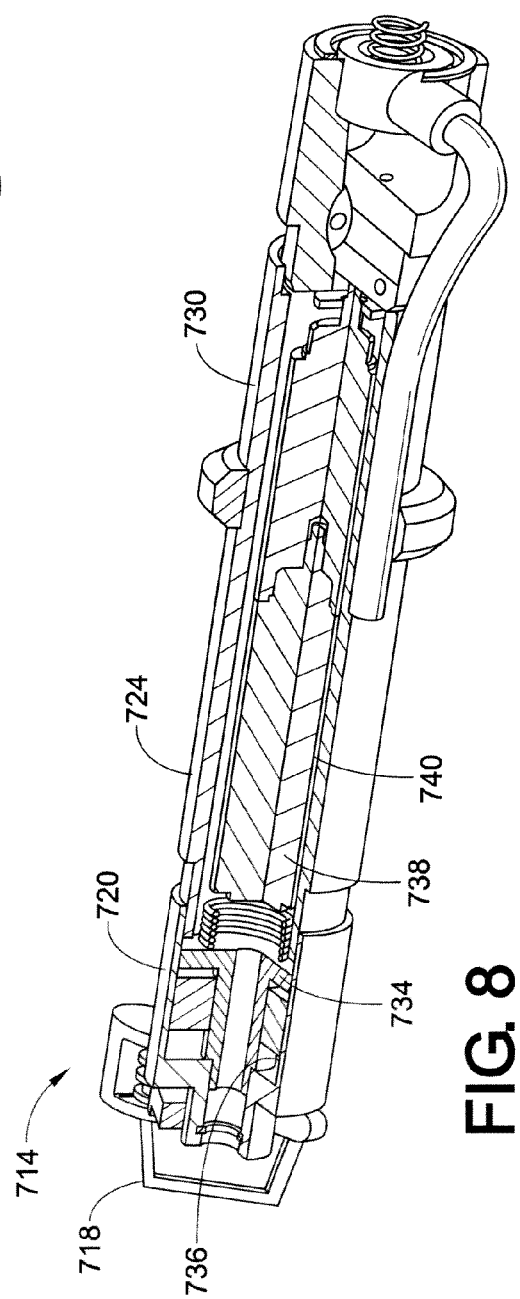

APPARATUS FOR MANIPULATION OF IMPLANTABLE MEDICAL DEVICE AND ASSOCIATED METHOD

BACKGROUND

This disclosure relates to an apparatus for manipulation of an implantable medical device and exemplary methods of using the apparatus to manipulate the implantable medical device in conjunction with a surgical procedure. For example, this disclosure describes exemplary embodiments for electrically-controlled rotational manipulation of a pacing lead to wind a helical tip of the pacing lead into an implant location until the pacing lead is seated. However, it will be appreciated that the disclosed concepts may have usefulness in manipulation of other implantable medical devices, such as other types of leads and therapy delivery tubes. Moreover, manipulation of the implantable medical device can also include unwinding the helical tip from the implant location as well as actuator-controlled grasping and releasing of the implantable medical device.

By way of background, electrical stimulation of body tissue and organs as a method of treating various pathological conditions is becoming quite commonplace. Such stimulation generally entails making some type of electrical contact with the body tissue or organ. In particular, with respect to the heart, electrical leads have been implanted by a thoracotomy in which an electrode formed on the end of the lead is physically implanted into the myocardial tissues.

Various electrode structures and various techniques for implanting electrode structures into such body tissue as the heart or myocardium, have been developed. Typically, electrodes attached to the heart are stimulated by a cardiac pacemaker which may be implanted within the patient's body.

Many medical electrode placement systems have been devised to assist in attaining accurate placement. Many of them utilize the principle of grasping an insulating head from which the electrode projects with an introducer, positioning the electrode appropriately, then releasing the head and withdrawing the tool.

A typical cardiac stimulating lead comprises an elongated lead body having a proximal and distal end. The lead body includes one or more flexible electrical conductors contained within a pliable, flexible insulating sheath. Suitable connectors are affixed to the proximal end of the conductors for facilitating attachment to an implantable or external electrical stimulating pulse generator. Affixed to the distal end of the lead body are one or more electrodes which are joined to the embedded conductor(s).

One known type of stimulating lead is the so-called myocardial screw-in lead. In this arrangement, one of the electrodes comprises a rigid helix having spaced-apart convolutions. It is supported by a molded plastic head, with the helix projecting perpendicularly from a surface of the head. The lead is installed using a specially designed tool which frictionally grasps the lead head, allowing the helix to be rotated into and anchored by the tissue to be stimulated. Thus, the tool is used much like a screw driver.

In the medical field, implantable leads are used with a wide variety of medical devices. For example, implantable leads are commonly used to form part of implantable cardiac pacemakers that provide therapeutic stimulation to the heart by sensing electrical activity of the heart and delivering pacing, cardioversion or defibrillation pulses via electrodes disposed on the leads, e.g., typically near distal ends of the leads. Leads may also be used to deliver therapeutic agents. A number of challenges exist with respect to medical leads; in particular, as more advanced and complex therapeutic techniques are developed, new configurations are required to facilitate fixation of lead electrodes at alternate implant sites within a patient.

It is desirable for a lead to be implanted with the center axis of the helical electrode normal to the surface of the heart. The existing rigid introducers often require a straight line between the point of entering the body and the implant position on the heart. This alignment is extremely challenging since the target spot is not directly visualized. Many or most traditional lead introducers are not suited for a minimally invasive (MI) approach due to their size and need for a straight-line approach. When leads must be placed on the superior portion of the left ventricle, as with resynchronization therapy, specialized tools and methods must be employed to reduce trauma to the patient and reach the appropriate location.

Based on the foregoing, a solution that simplifies manipulation of implantable medical devices, particularly rotational manipulation, is desirable. Additionally, a solution that that overcomes at least a portion of the drawbacks associated with current techniques for rotational manipulation of implantable medical devices is desirable.

SUMMARY

In one aspect, an apparatus for manipulation of an implantable medical device is provided. In one embodiment, the apparatus includes a surgical tool. In the embodiment being described, the surgical tool includes a mechanical interface that enables a surgical instrument to hold and position the surgical tool in conjunction with a surgical procedure, an electrical drive mechanism with a drive shaft, the electrical drive mechanism for selectively controlling bidirectional rotation of the drive shaft, and a grasping mechanism operationally coupled to the drive shaft such that rotation of the grasping mechanism is driven by the drive shaft, the grasping mechanism for releasably grasping the implantable medical device.

In another aspect, a method for manipulation of an implantable medical device is provided. In one embodiment, the method includes: a) providing a surgical device with a surgical tool comprising a mechanical interface, an electrical drive mechanism with a drive shaft, and a grasping mechanism operationally coupled to the drive shaft such that rotation of the grasping mechanism is driven by the drive shaft, the surgical device also including a controller in operative communication with the electrical drive mechanism and comprising a first control device; b) holding the surgical tool with a surgical instrument by grasping the mechanical interface; c) releasably grasping an implantable medical device with the grasping mechanism; d) positioning the surgical tool in conjunction with a surgical procedure using the surgical instrument; and e) selectively controlling the electrical drive mechanism to rotate the implantable medical device in a first direction in response to an implant activation of the first control device to wind a helical tip of the implantable medical device into an implant location until the implantable medical device is seated.

In yet another aspect, another embodiment of an apparatus for manipulation of an implantable medical device is provided. The apparatus includes a surgical tool and a controller. In the embodiment being described, the surgical tool includes a mechanical interface, an electrical drive mechanism, a grasping mechanism, and an actuator. The mechanical interface enables a surgical instrument to hold and position the surgical tool in conjunction with a surgical procedure. The electrical drive mechanism includes a drive shaft. The electrical drive mechanism for selectively controlling bidirectional rotation of the drive shaft. The grasping mechanism being operationally coupled to the drive shaft such that rotation of the grasping mechanism is driven by the drive shaft. In this embodiment, the grasping mechanism includes a plurality of jaws resiliently biased to a normally closed position for releasably grasping the implantable medical device. The actuator being operationally coupled to the plurality of jaws for selectively controlling a position of at least one jaw to move the plurality of jaws between the normally closed position and an open position. In the embodiment being described, the controller includes a first control device in operative communication with the electrical drive mechanism and a second control device in operative communication with the actuator. An implant activation of the first control device controls the electrical drive mechanism to rotate the grasping mechanism in a first direction and a removal activation of the first control device controls the electrical drive mechanism to rotate the grasping mechanism in a second direction opposite the first direction. An open activation of the second control device controls the actuator to open the plurality of jaws and a close activation of the second control device controls the actuator to allow the plurality of jaws to move toward the normally closed position.

Further scope of the applicability of the present invention will become apparent from the detailed description provided below. It should be understood, however, that the detailed description and specific examples, while indicating preferred embodiments of the invention, are given by way of illustration only, since various changes and modifications within the spirit and scope of the invention will become apparent to those skilled in the art.

DESCRIPTION OF THE DRAWINGS

The present invention exists in the construction, arrangement, and combination of the various parts of the device, and steps of the method, whereby the objects contemplated are attained as hereinafter more fully set forth, specifically pointed out in the claims, and illustrated in the accompanying drawings in which:

FIG. 7 shows a perspective view of an exemplary embodiment of a surgical tool;

FIG. 8 shows a cutaway view of the surgical tool of FIG. 7;

DETAILED DESCRIPTION

Various embodiments of a surgical device and associated methods of using the surgical device for manipulation of an implantable medical device in conjunction with a surgical procedure are disclosed herein. Generally, the surgical device includes a surgical tool and a controller. In certain embodiments, the surgical tool may be disposable. In other embodiments, the surgical tool may be reuseable or recyclable. In certain embodiments, the surgical tool may be cylindrical and relatively small. For example, surgical tool may be less than three inches in length and less than a half inch in width. In other embodiments, the surgical tool may be constructed to any suitable size and shape.

Figure 1:
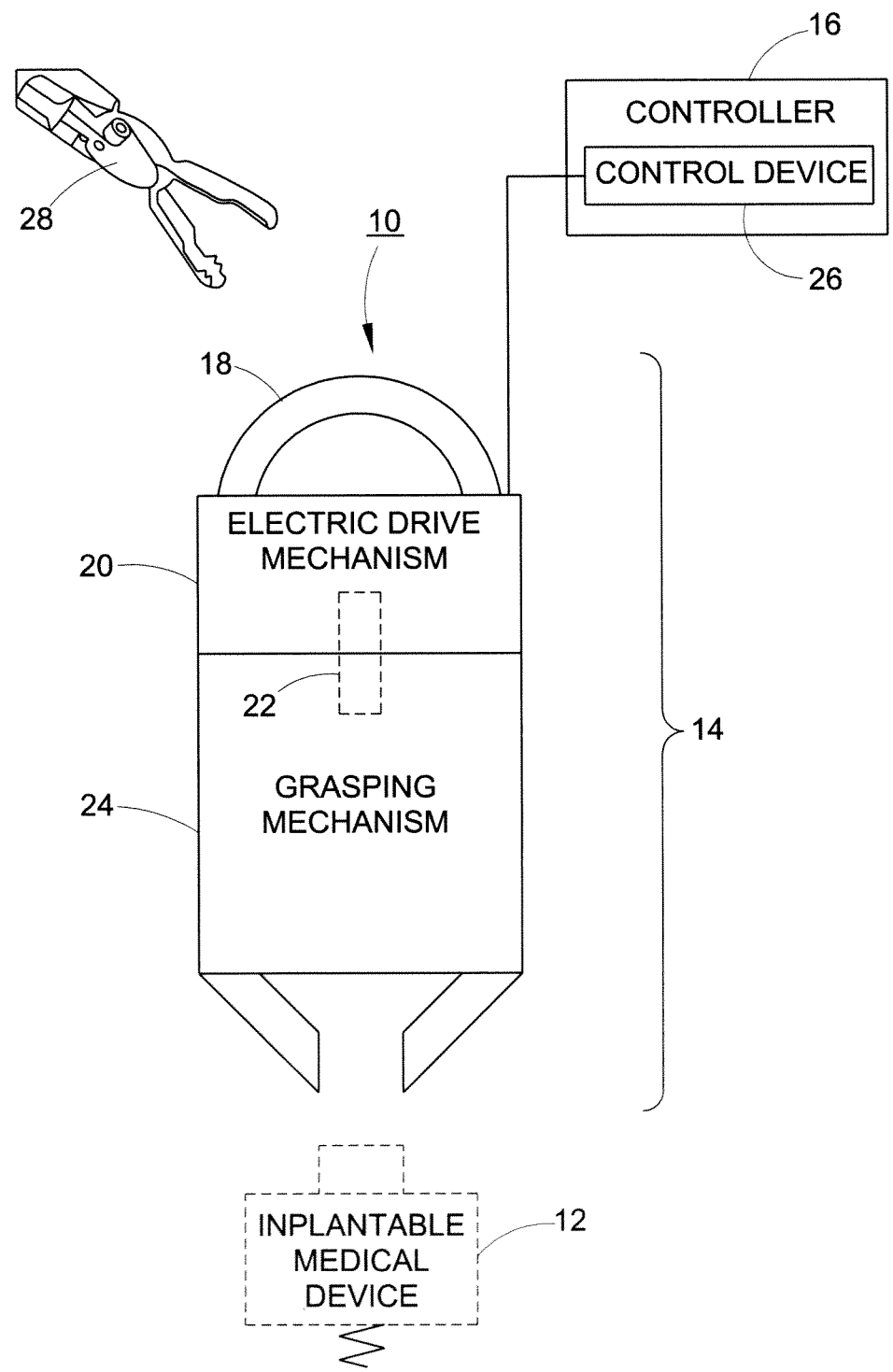
FIG. 1 is a block diagram of an exemplary embodiment of a surgical device.

Referring now to the drawings wherein the showings are for purposes of illustrating the exemplary embodiments only and not for purposes of limiting the claimed subject matter, FIG. 1 depicts an exemplary embodiment of a surgical device 10 for manipulation of an implantable medical device 12 may include a surgical tool 14 and a controller 16. The surgical tool 14 may include a mechanical interface 18, an electrical drive mechanism 20 with a drive shaft 22, and a grasping mechanism 24. The controller 16 may include a first control device 26.

The mechanical interface 18 may enable a surgical instrument 28 to hold and position the surgical tool 14 in conjunction with a surgical procedure. The electrical drive mechanism 20 may selectively control bidirectional rotation of the drive shaft 22. The grasping mechanism 24 may be operationally coupled to the drive shaft 22 such that rotation of the grasping mechanism 24 is driven by the drive shaft 22. The grasping mechanism 24 may releasably grasp the implantable medical device 12.

The first control device 26 may be in operative communication with the electrical drive mechanism 20. An implant activation of the first control device 26 may control the electrical drive mechanism 20 to rotate the grasping mechanism 24 in a first direction. A removal activation of the first control device 26 may control the electrical drive mechanism 20 to rotate the grasping mechanism 24 in a second direction opposite the first direction.

In various applications of the surgical device 10, the implantable medical device 12 may include a pacing lead, a stimulating lead, a sensing lead, a bipolar lead, a unipolar lead, a therapy delivery tube, a medication delivery tube, a cell delivery tube, a gene delivery tube, a stem cell delivery tube, or any similar implantable medical device. It is understood that a given implantable medical device may have more than one of the enumerated characteristics. For example, a pacing lead may also be referred to as a stimulating lead and may be bipolar or unipolar. Similarly, a therapy deliver tube may be used to deliver medication, cells, genes, or stem cells. With regard to cell-based therapy, the surgical device 10 may be used to deliver skeletal myoblasts, circulating endothelial progenitor cells, and other bone marrow-derived mononuclear cell populations as well as other progenitor and stem cell types, including embryonic stem cells (ESCs), hematopoietic stem cells, mesenchymal stem cells (MSCs), other endothelial progenitor cells, and cardiac stem cells.

In various embodiments of the surgical device 10, the mechanical interface 18 may include a handle, a loop, a hook, a raised ridge, an elongated protrusion, a socket, a connector, a coupling, or any suitable mechanical interface. It is understood that a given mechanical interface may have more than one of the enumerated characteristics. In one embodiment, the mechanical interface may be adapted to be grasped by the surgical instrument. In another embodiment, the mechanical interface may interconnect with a mating mechanical interface on the surgical instrument.

In various applications of the surgical device 10, the surgical instrument 28 may include a robotic surgical system, a forceps instrument, a grasper instrument, a thoracoscopic instrument, a laparoscopic instrument, or any suitable surgical instrument. The da Vinci® Surgical System by Intuitive Surgical, Inc. of Sunnyvale, Calif. is an example of a commercially available robotic surgical system. It is understood that a given surgical instrument may have more than one of the enumerated characteristics. For example, a robotic surgical system may use forceps or grasper accessories. Similarly, a thoracoscopic instrument may include a forceps or grasper.

In various applications of the surgical device 10, the surgical procedure may include an MI procedure, a thoracoscopic procedure, a laparoscopic procedure, or any similar surgical procedure. In various embodiments of the surgical device 10, the electrical drive mechanism 20 may include a servo motor, a stepper motor, or any suitable electrical motor. The drive shaft 22 may be directly driven by the motor. Alternatively, the electrical drive mechanism 20 may include a gear reduction assembly or any suitable non-direct drive assembly between the motor and the drive shaft 22.

In various embodiments of the surgical device 10, the first control device 26 may include a three-position toggle switch, a three-position rotary switch, a three-position slide switch, a three-position return-to-center switch, a single axis joystick, a set of two momentary switches, a set of two two-position switches, a foot switch, a peddle switch, or any suitable control device. The three-position toggle switch, for example, may have an off position, an implant position, and a removal position. The set of two two-position switches, for example, may include a first switch with an implant position and a removal position and a second switch with an on position and an off position.

In various embodiments of the surgical device 10, the controller 16 and first control device 26 may include various electrical components suitably connected via discrete wiring. In another embodiment, the controller 16 and first control device 26 may include various electrical or electronic components suitably connected via a circuit card assembly.

In various embodiments of the surgical device 10, the controller 16 and first control device 26 may include a power module, a power distribution circuit, a processor, a memory, a storage device, one or more indicator for showing status or sensed operating conditions for the electrical drive mechanism 20, a display device for showing status or sensed operating conditions for the electrical drive mechanism 20, a closed loop controller circuit for feedback control of the electrical drive mechanism 20, a driver circuit providing drive signals to the electrical drive mechanism 20, and a transceiver circuit for communicating with the electrical drive mechanism 20. The power module may include a battery or an adapter to receive standard utility power or another form of electrical power from an external power supply. In this arrangement, the controller 16 may distribute power to any components in the surgical tool 14 needing power via a cable. The cable may also carry drive and control signals for operation of the electrical drive mechanism 20.

In yet another embodiment of the surgical device 10, the controller 16 may be wirelessly coupled to the electrical drive mechanism 20. Wireless communication may implement Bluetooth or any suitable wireless communication protocol. In this arrangement, the surgical tool 14 may include a battery or another suitable power source for operation of the electrical drive mechanism 20 and a transceiver circuit for communicating drive and control signals with the controller 16.

In one embodiment, the controller 16 may continue to control the electrical drive mechanism 20 to rotate the grasping mechanism 24 in the first direction until the implant activation is selectively released. In another embodiment, the controller 16 may control the electrical drive mechanism 20 such that the grasping mechanism 24 is automatically rotated a predetermined amount of revolutions in response to the implant activation. The predetermined amount may be based at least in part on the revolutions needed to wind a helical tip of the implantable medical device 12 into an implant location until the implantable medical device 12 is seated. For example, a given implantable medical device may be seated after two revolutions, two and a half revolutions, three revolutions, or any suitable amount of revolutions needed based on the helical tip. In one embodiment, the surgical tool 14 may include mechanical stops to limit the rotational movement to the predetermined amount of revolutions. The mechanical stops may be adjustable for compatibility with multiple types of implantable medical devices. In another embodiment, the surgical tool 14 may include sensors to detect rotational movement, revolutions, or position of the grasping mechanism 24 to provide corresponding signals to the controller 16 or first control device 26.

In one embodiment, the controller 16 may continue to control the electrical drive mechanism 20 to rotate the grasping mechanism 24 in the second direction until the removal activation is selectively released. In another embodiment, the controller 16 may control the electrical drive mechanism 20 such that the grasping mechanism 24 is automatically rotated a predetermined amount of revolutions in response to the removal activation. The predetermined amount being based at least in part on the revolutions needed to unwind a helical tip of the implantable medical device 12 from an implant location when the implantable medical device 12 is seated at the implant location. For example, a given helical tip may be unwound from the implant location after two revolutions, two and a half revolutions, three revolutions, or any suitable amount of revolutions needed based on the helical tip. As described above for the implant activation, surgical tool 14 may include may include mechanical stops, sensors, or a combination thereof in conjunction with limiting rotational movement to the predetermined amount of revolutions for the removal activation.

Figure 2:
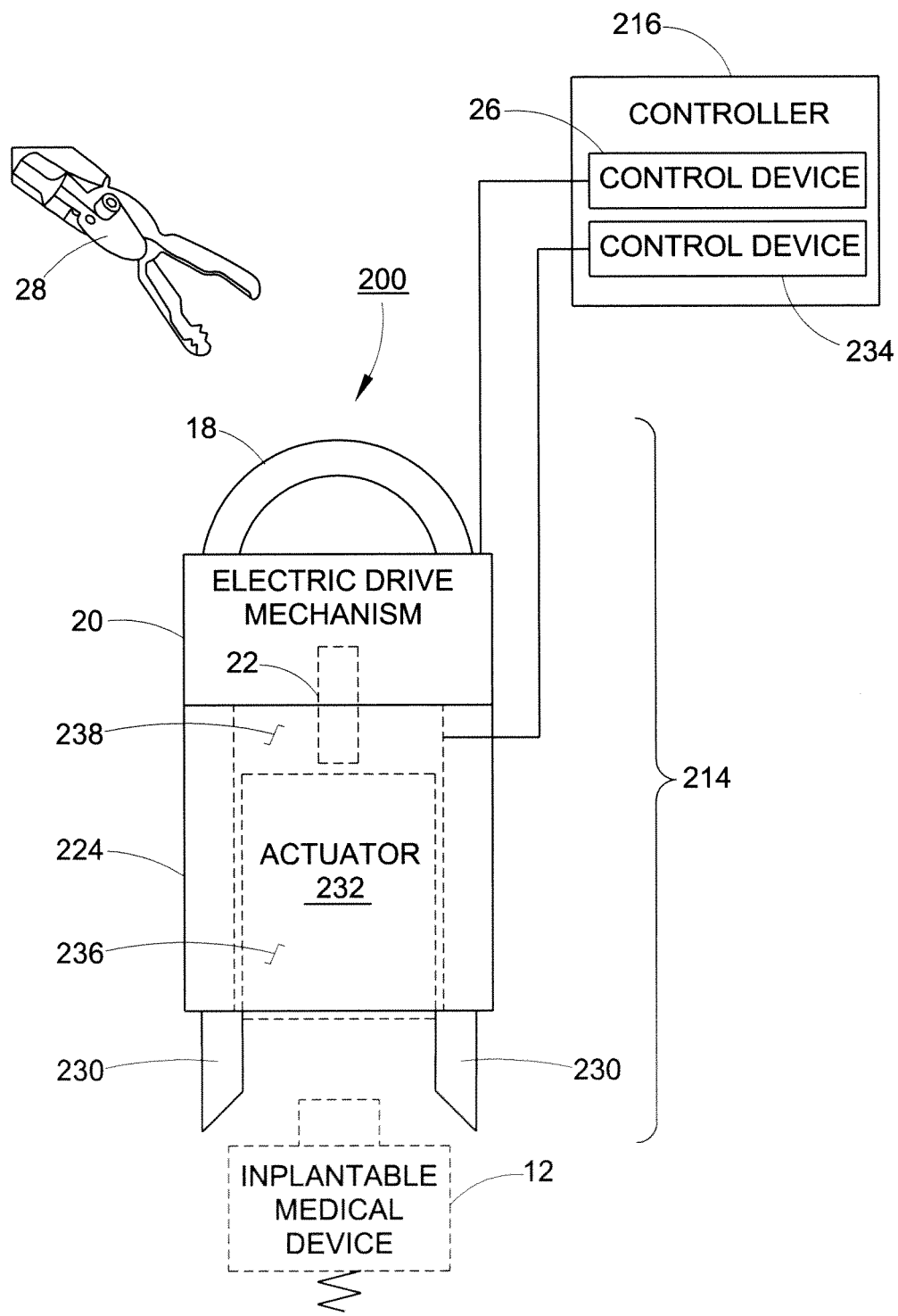
FIG. 2 is a block diagram of another exemplary embodiment of a surgical device showing jaws of a grasping mechanism in an open position.

With reference to FIG. 2, another exemplary embodiment of a surgical device 200 for manipulation of an implantable medical device 12 may include a surgical tool 214 and a controller 216. The surgical tool 214 may include a mechanical interface 18, an electrical drive mechanism 20 with a drive shaft 22, and a grasping mechanism 224. The grasping mechanism 224 may include two or more jaws 230. The surgical tool may also include an actuator 232. The controller 216 may include a first control device 26 and a second control device 234. The implantable medical device 12, mechanical interface 18, electrical drive mechanism 20, drive shaft 22, and first control device 26 are described above in conjunction with the surgical device 10 of FIG. 1.

In the embodiment being described, the jaws 230 may be resiliently biased to a normally closed position for releasably grasping the implantable medical device 12. The actuator 232 may be operationally coupled to the jaws 230 for selectively controlling the jaws 230 between the normally closed position and an open position. The jaws 230 are shown in an open position.

The second control device 234 may be in operative communication with the actuator 232. An open activation of the second control device 234 may control the actuator 232 to open the jaws 230. A close activation of the second control device 234 may control the actuator 232 to allow the jaws 230 to move toward the normally closed position. See U.S. Patent Application Publication No. 2005/0004644 to Kelsch et al. for additional arrangements of jaws 230 that could be used in the grasping mechanism 224. The contents of U.S. Patent Application Publication No. 2005/0004644 are fully incorporated herein by reference.

In another embodiment of the surgical device 200, the jaws 230 may include at least one stationary jaw and at least one adjustable jaw. Each stationary jaw may have a fixed position in relation to the normally closed position and the open position. Each adjustable jaw may be resiliently biased to the normally closed position and adjustably controlled by the actuator 232 between the normally closed position and the open position.

In various embodiments of the surgical device 200, the grasping mechanism 224 may include at least one spring resiliently biasing the jaws 230 to the normally closed position. In various embodiments of the surgical device 200, the actuator 232 may include a pneumatic actuator, a linear actuator, a servo actuator, a linear motor, a servo motor, a stepper motor, or any suitable actuator.

In various embodiments of the surgical device 200, the second control device 234 may include a squeeze bulb, a toggle switch, a rotary switch, a slide switch, a single axis joystick, a momentary switch, a foot switch, a peddle switch, or any suitable control device. The squeeze bulb, for example, may have an open position corresponding to a squeeze and a close position corresponding to releasing the squeeze or opening a release valve. The toggle switch, for example, may have an open position and a close position.

In another embodiment, the actuator 232 may include a pneumatic actuator formed by a piston 236 within a cylinder 238. The piston 236 may be adjustably controlled by the second control device 234 between a recessed position and an extended position. In FIG. 2, the piston 236 is shown in the extended position. The piston 236 may be resiliently biased within the cylinder 238 to the recessed position. The piston 236 may engage the jaws 230 at a predetermined location between the recessed position and the extended position such that when the piston 236 is at the extended position the jaws 230 are at the open position. Additionally, the piston 236 may engage the drive shaft 22 at the recessed position to enable rotational movement of the grasping mechanism 224 when the jaws 230 are in the normally closed position. The piston 236 may disengage from the drive shaft 22 when moved toward the extended position to disable rotational movement of the grasping mechanism 224 when the jaws 230 are not in the normally closed position.

In various embodiments, the actuator 232 may be arranged to rotate with the grasping mechanism 224 when the electrical drive mechanism 20 is activated or to remain stationary with the electrical drive mechanism 20 when the electrical drive mechanism 20 is activated. FIG. 2 shows an arrangement where actuator 232 may rotate with the grasping mechanism 224. In an alternate arrangement (see FIGS. 7-12), the actuator 232 may be disposed proximate to the mechanical interface 18 of the surgical tool 214. In this embodiment, the electrical drive mechanism 224 may include a sleeve that slides over a drive unit. The sleeve may move in concert with the piston to form a linkage or drive train to operate the grasping mechanism 224. In other embodiments, push rods or any suitable linkage or drive train components may be used in place of the sleeve.

In the embodiment being described, the second control device 234 may include a squeeze bulb in fluidic communication with the cylinder 238. The open activation may occur in response to the squeeze bulb being activated one or more times to compress air into the cylinder 238 to move the piston 236 from the recessed position toward the extended position. The second control device 234 in this embodiment may also include a release valve in fluidic communication with the cylinder 238. The close activation may occur in response to the release valve being activated to release compressed air from the cylinder 238 to allow the piston 236 to move toward the recessed position.

In various embodiments of the surgical device 200, the controller 216 and second control device 234 may include various electrical components suitably connected via discrete wiring. In another embodiment, the controller 216 and second control device 234 may include various electrical or electronic components suitably connected via a circuit card assembly.

In various embodiments of the surgical device 200, the controller 216 and second control device 234 may include a power module, a power distribution circuit, a processor, a memory, a storage device, one or more indicator for showing status or sensed operating conditions for the actuator 232, a display device for showing status or sensed operating conditions for the actuator 232, a closed loop controller circuit for feedback control of the actuator 232, a driver circuit providing drive signals to the actuator 232, and a transceiver circuit for communicating with the actuator 232. The power module may include a battery or an adapter to receive standard utility power or another form of electrical power from an external power supply. In this arrangement, the controller 216 may distribute power to any components in the surgical tool 214 needing power via a cable. The cable may also carry drive and control signals for operation of the surgical tool 214.

In yet another embodiment of the surgical device 200, the controller 216 may be wirelessly coupled to the actuator 232. Wireless communication may implement Bluetooth or any suitable wireless communication protocol. In this arrangement, the surgical tool 214 may include a battery or another suitable power source for operation of the actuator 232 and a transceiver circuit for communicating drive and control signals with the controller 216.

In one embodiment, the controller 216 may continue to control the actuator 232 to move the jaws 230 toward the open position until the open activation is selectively released. In another embodiment, the controller 216 may control the actuator 232 such that the jaws 230 are automatically moved to the open position in response to the open activation.

In one embodiment, the controller 216 may continue to control the actuator 232 to move the jaws 230 toward the normally closed position until the close activation is selectively released. In another embodiment, the controller 216 may control the actuator 232 such that the jaws are automatically moved to the close position in response to the close activation. In yet another embodiment, the controller 216 controls the actuator 232 such that the close activation occurs in response to selective release of the open activation.

Figure 3:
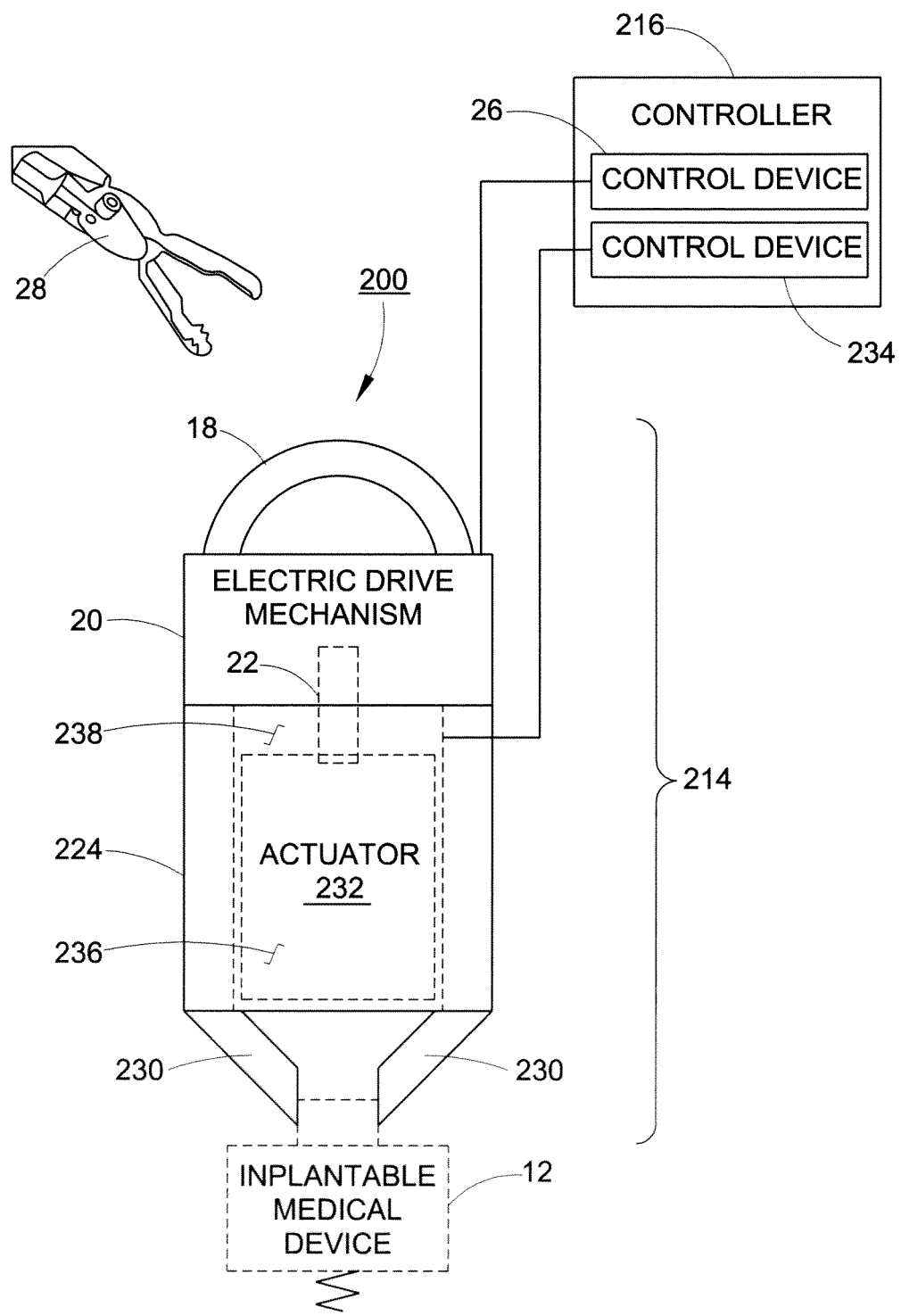
FIG. 3 shows the surgical device of FIG. 2 with the jaws of the grasping mechanism in a normally closed position.

With reference to FIG. 3, the surgical device 200 of FIG. 2 is shown with the jaws 230 of the grasping mechanism 224 in the normally closed position. The actuator 232 is shown in the recessed position and the jaws 230 are releasably grasping the implantable medical device 12. As shown, in the recessed position, the actuator 232 may engage the drive shaft 22 to enable rotational movement of the grasping mechanism 224.

Figure 4:
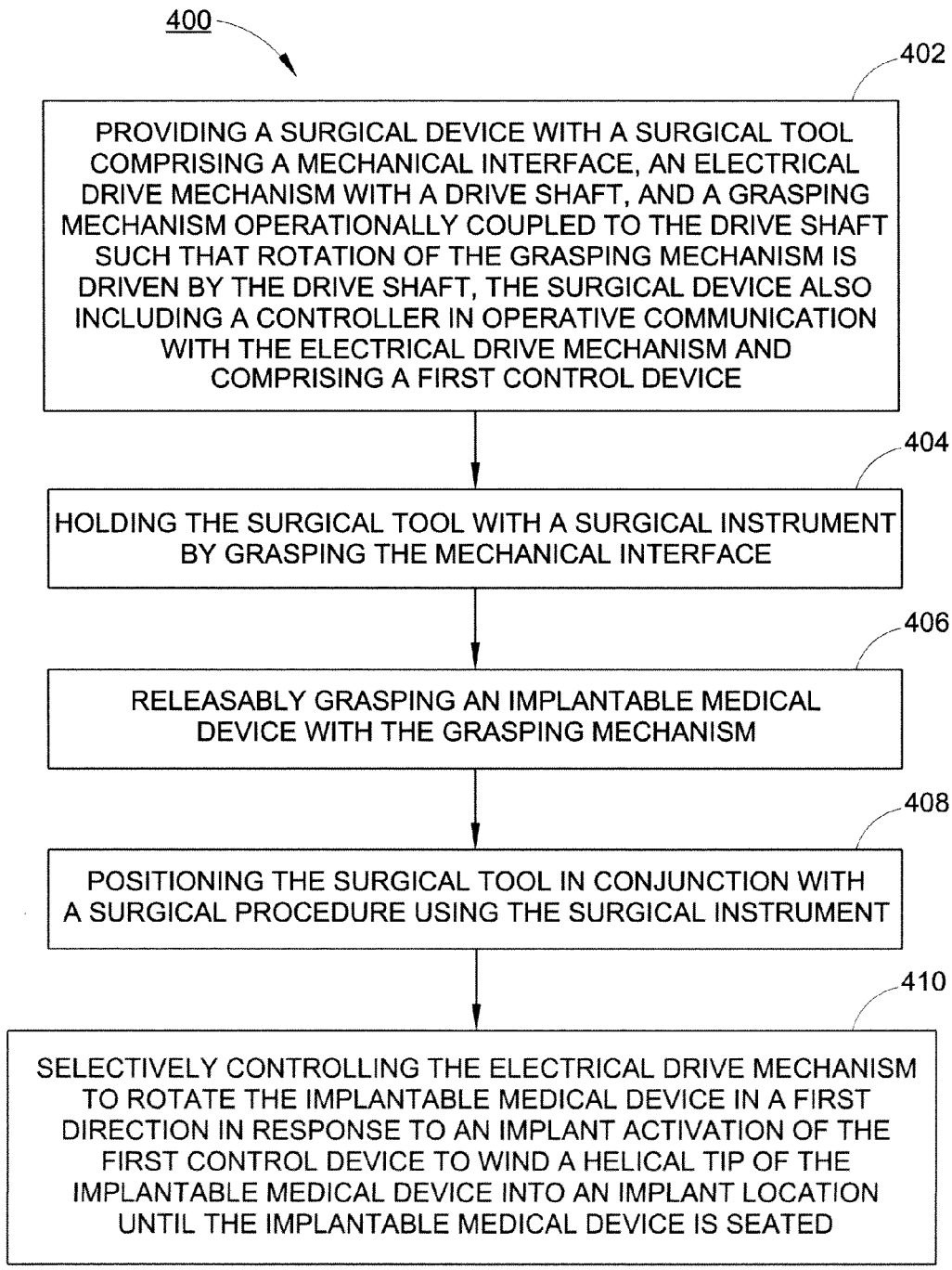
FIG. 4 is a flow chart of an exemplary embodiment of a process for manipulating an implantable medical device.

With reference to FIG. 4, an exemplary embodiment of a process 400 for manipulation of an implantable medical device begins at 402 where a surgical device with a surgical tool may be provided. The surgical tool may include a mechanical interface, an electrical drive mechanism with a drive shaft, and a grasping mechanism operationally coupled to the drive shaft such that rotation of the grasping mechanism is driven by the drive shaft. The surgical device may also include a controller with a first control device in operative communication with the electrical drive mechanism.

At 404, the surgical tool may be held with a surgical instrument by grasping the mechanical interface. Next, an implantable medical device may be releasably grasped with the grasping mechanism (406). At 408, the surgical tool may be positioned in conjunction with a surgical procedure using the surgical instrument. Next, the electrical drive mechanism may be selectively controlled to rotate the implantable medical device in a first direction in response to an implant activation of the first control device to wind a helical tip of the implantable medical device into an implant location until the implantable medical device is seated (410).

In another embodiment, the process 400 may also include continuing to control the electrical drive mechanism to rotate the implantable medical device in the first direction until the implant activation of the first control device is selectively released. In yet another embodiment of the process 400, the controller may control the electrical drive mechanism such that the implantable medical device is automatically rotated a predetermined amount of revolutions in response to the implant activation. In this embodiment, the predetermined amount may be based at least in part on the revolutions needed to wind the helical tip into the implant location until the implantable medical device is seated. In still another embodiment, the process 400 may also include selectively releasing the implantable medical device from the grasping mechanism.

In still yet another embodiment, the process 400 may also include selectively controlling the electrical drive mechanism to rotate the implantable medical device in a second direction opposite the first direction in response to a removal activation of the first control device to unwind the helical tip from the implant location. In this embodiment, the process 400 may further include continuing to control the electrical drive mechanism to rotate the implantable medical device in the second direction until the removal activation is selectively released. Alternatively, in the embodiment of the 400 being described, the controller may control the electrical drive mechanism such that the implantable medical device is automatically rotated a predetermined amount of revolutions in response to the removal activation. In this embodiment, the predetermined amount may be based at least in part on the revolutions needed to unwind the helical tip from the implant location when the implantable medical device is seated at the implant location.

In various applications of the process 400, the implantable medical device may include a pacing lead, a stimulating lead, a sensing lead, a bipolar lead, a unipolar lead, a therapy delivery tube, a medication delivery tube, a cell delivery tube, a gene delivery tube, a stem cell delivery tube, or any similar implantable medical device. It is understood that a given implantable medical device may have more than one of the enumerated characteristics. For example, a pacing lead may also be referred to as a stimulating lead and may be bipolar or unipolar. Similarly, a therapy deliver tube may be used to deliver medication, cells, genes, or stem cells. With regard to cell-based therapy, the surgical device 10 may be used to deliver skeletal myoblasts, circulating endothelial progenitor cells, and other bone marrow-derived mononuclear cell populations as well as other progenitor and stem cell types, including embryonic stem cells (ESCs), hematopoietic stem cells, mesenchymal stem cells (MSCs), other endothelial progenitor cells, and cardiac stem cells.

In various embodiments of the process 400, the mechanical interface may include a handle, a loop, a hook, a raised ridge, an elongated protrusion, a socket, a connector, a coupling, or any suitable mechanical interface. It is understood that a given mechanical interface may have more than one of the enumerated characteristics. In one embodiment, the mechanical interface may be adapted to be grasped by the surgical instrument. In another embodiment, the mechanical interface may interconnect with a mating mechanical interface on the surgical instrument.

In various applications of the process 400, the surgical instrument may include a robotic surgical system, a forceps instrument, a grasper instrument, a thoracoscopic instrument, a laparoscopic instrument, or any suitable surgical instrument. The da Vinci® Surgical System by Intuitive Surgical, Inc. of Sunnyvale, Calif. is an example of a commercially available robotic surgical system. It is understood that a given surgical instrument may have more than one of the enumerated characteristics. For example, a robotic surgical system may use forceps or grasper accessories. Similarly, a thoracoscopic instrument may include a forceps or grasper.

In various applications of the process 400, the surgical procedure may include an MI procedure, a thoracoscopic procedure, a laparoscopic procedure, or any similar surgical procedure. In various embodiments of the process 400, the electrical drive mechanism may include a servo motor, a stepper motor, or any suitable electrical motor. The drive shaft may be directly driven by the motor. Alternatively, the electrical drive mechanism may include a gear reduction assembly or any suitable non-direct drive assembly between the motor and the drive shaft.

In various embodiments of the process 400, the first control device may include a three-position toggle switch, a three-position rotary switch, a three-position slide switch, a three-position return-to-center switch, a single axis joystick, a set of two momentary switches, a set of two two-position switches, a foot switch, a peddle switch, or any suitable control device. The three-position toggle switch, for example, may have an off position, an implant position, and a removal position. The set of two two-position switches, for example, may include a first switch with an implant position and a removal position and a second switch with an on position and an off position.

In various embodiments of the process 400, the controller and first control device may include various electrical components suitably connected via discrete wiring. In another embodiment, the controller and first control device may include various electrical or electronic components suitably connected via a circuit card assembly.

In various embodiments of the process 400, the controller and first control device may include a power module, a power distribution circuit, a processor, a memory, a storage device, one or more indicator for showing status or sensed operating conditions for the electrical drive mechanism, a display device for showing status or sensed operating conditions for the electrical drive mechanism, a closed loop controller circuit for feedback control of the electrical drive mechanism, a driver circuit providing drive signals to the electrical drive mechanism, and a transceiver circuit for communicating with the electrical drive mechanism. The power module may include a battery or an adapter to receive standard utility power or another form of electrical power from an external power supply. In this arrangement, the controller may distribute power to any components in the surgical tool needing power via a cable. The cable may also carry drive and control signals for operation of the electrical drive mechanism.

In yet another embodiment of the process 400, the controller may be wirelessly coupled to the electrical drive mechanism. Wireless communication may implement Bluetooth or any suitable wireless communication protocol. In this arrangement, the surgical tool may include a battery or another suitable power source for operation of the electrical drive mechanism and a transceiver circuit for communicating drive and control signals with the controller.

Figure 5:
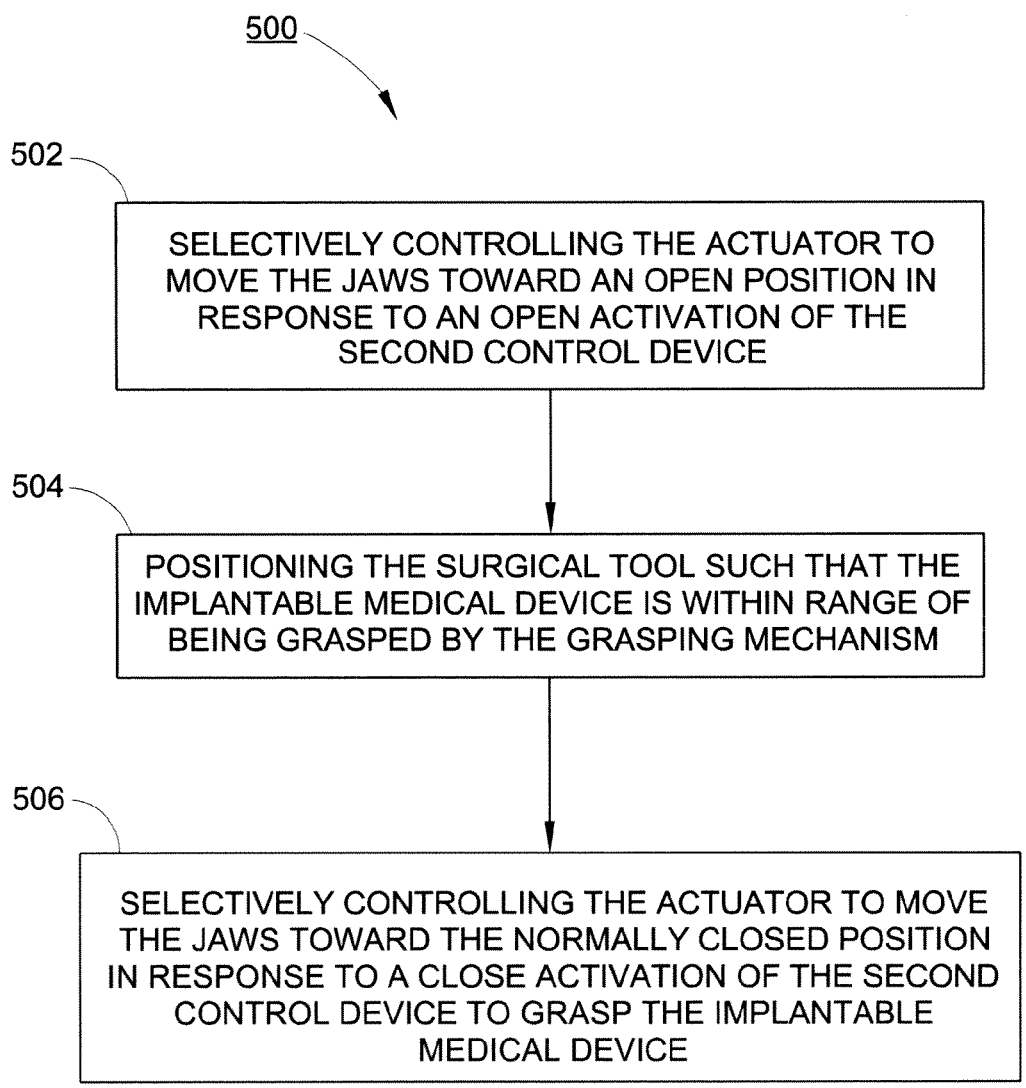
FIG. 5, in conjunction with FIG. 4, is a flow chart of another exemplary embodiment of a process for manipulating an implantable medical device.

With reference to FIG. 5, in another exemplary embodiment of the process 500, the grasping mechanism may include two or more jaws resiliently biased to a normally closed position and the surgical tool may include an actuator operationally coupled to the jaws. In this embodiment, the controller may also include a second control device in operative communication with the actuator. The process 500 may include selectively controlling the actuator to move the jaws toward an open position in response to an open activation of the second control device (502) in addition to 402, 404, 406, 408, and 410 of FIG. 4. At 504, the surgical tool may be positioned such that the implantable medical device is within range of being grasped by the grasping mechanism. Next, the actuator may be selectively controlled to move the jaws toward the normally closed position in response to a close activation of the second control device to grasp the implantable medical device (506).

In another embodiment, the process 500 may also include continuing to control the actuator to move the jaws toward the open position until the open activation of the second control device is selectively released. In yet another embodiment of the process 500, the controller may control the actuator such that the jaws are automatically moved to the open position in response to the open activation.

In still yet another embodiment, the process 500 may also include continuing to control the actuator to move the jaws toward the normally closed position until the close activation of the second control device is selectively released. In another embodiment of the process 500, the controller may control the actuator such that the jaws are automatically moved to the close position in response to the close activation. In yet another embodiment of the process 500, the controller may control the actuator such that the close activation occurs in response to selective release of the open activation.

In various embodiments of the process 500, the actuator may include a pneumatic actuator, a linear actuator, a servo actuator, a linear motor, a servo motor, a stepper motor, or any suitable actuator. In various embodiments of the process 500, the second control device may include a squeeze bulb, a toggle switch, a rotary switch, a slide switch, a single axis joystick, a momentary switch, a foot switch, a peddle switch, or any suitable control device. The squeeze bulb, for example, may have an open position corresponding to a squeeze and a close position corresponding to releasing the squeeze or opening a release valve. The toggle switch, for example, may have an open position and a close position.

In various embodiments of the process 500, the controller and second control device may include various electrical components suitably connected via discrete wiring. In another embodiment, the controller and second control device may include various electrical or electronic components suitably connected via a circuit card assembly.

In various embodiments of the process 500, the controller and second control device may include a power module, a power distribution circuit, a processor, a memory, a storage device, one or more indicator for showing status or sensed operating conditions for the actuator, a display device for showing status or sensed operating conditions for the actuator, a closed loop controller circuit for feedback control of the actuator, a driver circuit providing drive signals to the actuator, and a transceiver circuit for communicating with the actuator. The power module may include a battery or an adapter to receive standard utility power or another form of electrical power from an external power supply. In this arrangement, the controller may distribute power to any components in the surgical tool needing power via a cable. The cable may also carry drive and control signals for operation of the surgical tool.

In yet another embodiment of the process 500, the controller may be wirelessly coupled to the actuator. Wireless communication may implement Bluetooth or any suitable wireless communication protocol. In this arrangement, the surgical tool may include a battery or another suitable power source for operation of the actuator and a transceiver circuit for communicating drive and control signals with the controller.

Figure 6:
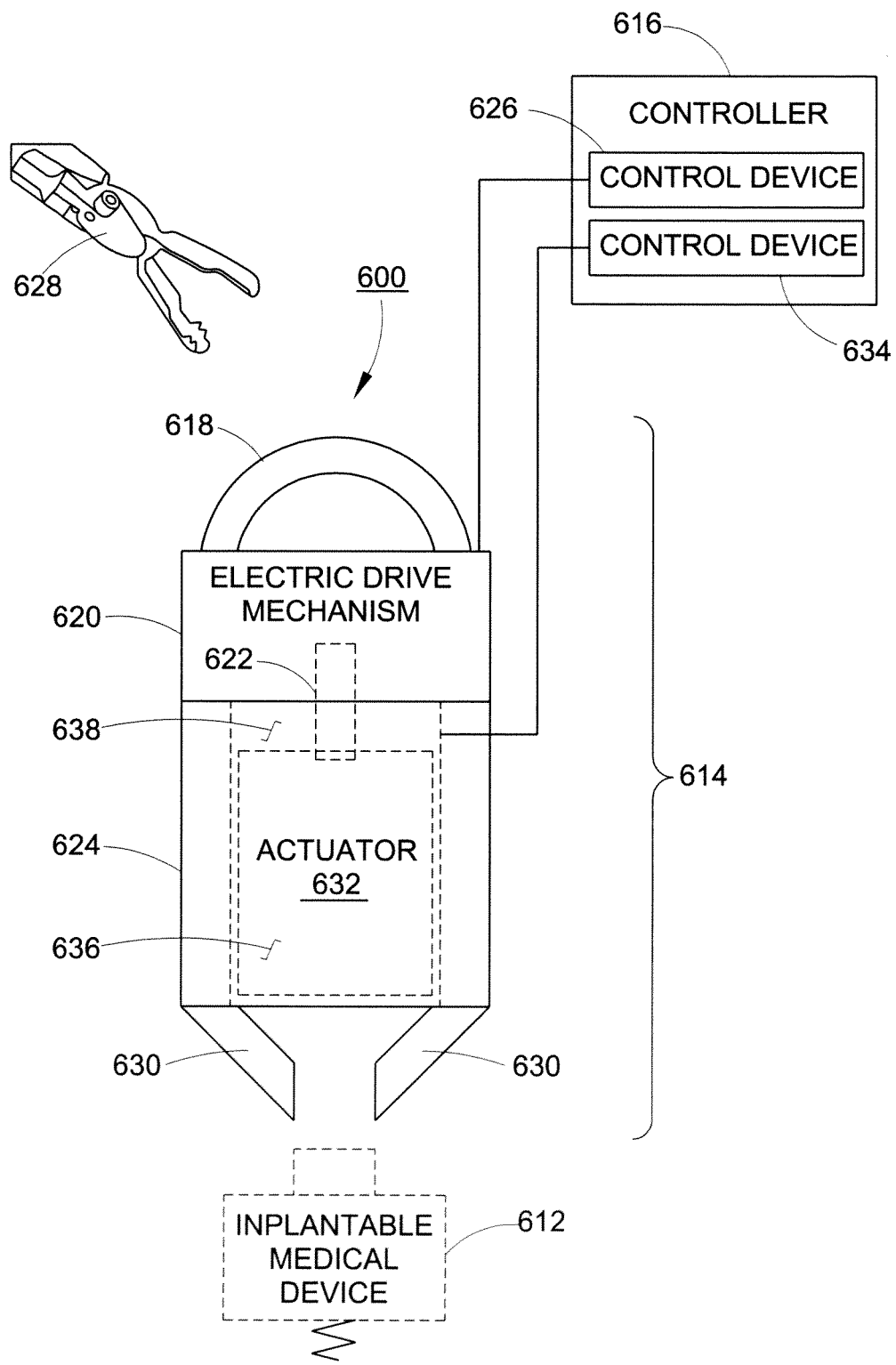
FIG. 6 is a block diagram of yet another exemplary embodiment of a surgical device.

With reference to FIG. 6, another exemplary embodiment of a surgical device 600 for manipulation of an implantable medical device 612 may include a surgical tool 614 and a controller 616. The surgical tool 614 may include a mechanical interface 618, an electrical drive mechanism 620 with a drive shaft 622, and a grasping mechanism 624. The grasping mechanism 624 may include two or more jaws 630. The surgical tool 614 may also include an actuator 632. The controller 616 may include a first control device 626 and a second control device 634.

The mechanical interface 618 may enable a surgical instrument 628 to hold and position the surgical tool 614 in conjunction with a surgical procedure. The electrical drive mechanism 620 may selectively control bidirectional rotation of the drive shaft 622. The grasping mechanism 624 may be operationally coupled to the drive shaft 22 such that rotation of the grasping mechanism 624 is driven by the drive shaft 622.

The jaws 630 may be resiliently biased to a normally closed position for releasably grasping the implantable medical device 612. The actuator 632 may be operationally coupled to the jaws 630 for selectively controlling the jaws 630 between the normally closed position and an open position.

The first control device 626 may be in operative communication with the electrical drive mechanism 620. An implant activation of the first control device 626 may control the electrical drive mechanism 620 to rotate the grasping mechanism 624 in a first direction. A removal activation of the first control device 626 may control the electrical drive mechanism 620 to rotate the grasping mechanism 624 in a second direction opposite the first direction.

The second control device 634 may be in operative communication with the actuator 632. An open activation of the second control device 634 may control the actuator 632 to open the jaws 630. A close activation of the second control device 634 may control the actuator 632 to allow the jaws 630 to move toward the normally closed position.

In various applications of the surgical device 600, the implantable medical device 612 may include a pacing lead, a stimulating lead, a sensing lead, a bipolar lead, a unipolar lead, a therapy delivery tube, a medication delivery tube, a cell delivery tube, a gene delivery tube, a stem cell delivery tube, or any similar implantable medical device. It is understood that a given implantable medical device may have more than one of the enumerated characteristics. For example, a pacing lead may also be referred to as a stimulating lead and may be bipolar or unipolar. Similarly, a therapy deliver tube may be used to deliver medication, cells, genes, or stem cells. With regard to cell-based therapy, the surgical device 10 may be used to deliver skeletal myoblasts, circulating endothelial progenitor cells, and other bone marrow-derived mononuclear cell populations as well as other progenitor and stem cell types, including embryonic stem cells (ESCs), hematopoietic stem cells, mesenchymal stem cells (MSCs), other endothelial progenitor cells, and cardiac stem cells.

In various embodiments of the surgical device 600, the mechanical interface 618 may include a handle, a loop, a hook, a raised ridge, an elongated protrusion, a socket, a connector, a coupling, or any suitable mechanical interface. It is understood that a given mechanical interface may have more than one of the enumerated characteristics. In one embodiment, the mechanical interface may be adapted to be grasped by the surgical instrument. In another embodiment, the mechanical interface may interconnect with a mating mechanical interface on the surgical instrument.

In various applications of the surgical device 600, the surgical instrument 628 may include a robotic surgical system, a forceps instrument, a grasper instrument, a thoracoscopic instrument, a laparoscopic instrument, or any suitable surgical instrument. The da Vinci® Surgical System by Intuitive Surgical, Inc. of Sunnyvale, Calif. is an example of a commercially available robotic surgical system. It is understood that a given surgical instrument may have more than one of the enumerated characteristics. For example, a robotic surgical system may use forceps or grasper accessories. Similarly, a thoracoscopic instrument may include a forceps or grasper.

In various applications of the surgical device 600, the surgical procedure may include an MI procedure, a thoracoscopic procedure, a laparoscopic procedure, or any similar surgical procedure. In various embodiments of the surgical device 600, the electrical drive mechanism 620 may include a servo motor, a stepper motor, or any suitable electrical motor. The drive shaft 622 may be directly driven by the motor. Alternatively, the electrical drive mechanism 620 may include a gear reduction assembly or any suitable non-direct drive assembly between the motor and the drive shaft 622.

In various embodiments of the surgical device 600, the first control device 626 may include a three-position toggle switch, a three-position rotary switch, a three-position slide switch, a three-position return-to-center switch, a single axis joystick, a set of two momentary switches, a set of two two-position switches, a foot switch, a peddle switch, or any suitable control device. The three-position toggle switch, for example, may have an off position, an implant position, and a removal position. The set of two two-position switches, for example, may include a first switch with an implant position and a removal position and a second switch with an on position and an off position.

In various embodiments of the surgical device 600, the controller 616 and first control device 626 may include various electrical components suitably connected via discrete wiring. In another embodiment, the controller 616 and first control device 626 may include various electrical or electronic components suitably connected via a circuit card assembly.

In various embodiments of the surgical device 600, the controller 616 and first control device 626 may include a power module, a power distribution circuit, a processor, a memory, a storage device, one or more indicator for showing status or sensed operating conditions for the electrical drive mechanism 620, a display device for showing status or sensed operating conditions for the electrical drive mechanism 620, a closed loop controller circuit for feedback control of the electrical drive mechanism 620, a driver circuit providing drive signals to the electrical drive mechanism 620, and a transceiver circuit for communicating with the electrical drive mechanism 620. The power module may include a battery or an adapter to receive standard utility power or another form of electrical power from an external power supply. In this arrangement, the controller 616 may distribute power to any components in the surgical tool 614 needing power via a cable. The cable may also carry drive and control signals for operation of the electrical drive mechanism 620.

In yet another embodiment of the surgical device 610, the controller 616 may be wirelessly coupled to the electrical drive mechanism 620. Wireless communication may implement Bluetooth or any suitable wireless communication protocol. In this arrangement, the surgical tool 614 may include a battery or another suitable power source for operation of the electrical drive mechanism 620 and a transceiver circuit for communicating drive and control signals with the controller 616.

In one embodiment, the controller 616 may continue to control the electrical drive mechanism 620 to rotate the grasping mechanism 624 in the first direction until the implant activation is selectively released. In another embodiment, the controller 616 may control the electrical drive mechanism 620 such that the grasping mechanism 624 is automatically rotated a predetermined amount of revolutions in response to the implant activation. The predetermined amount may be based at least in part on the revolutions needed to wind a helical tip of the implantable medical device 612 into an implant location until the implantable medical device 612 is seated. In one embodiment, the surgical tool 614 may include mechanical stops to limit the rotational movement to the predetermined amount of revolutions. The mechanical stops may be adjustable for compatibility with multiple types of implantable medical devices. In another embodiment, the surgical tool 614 may include sensors to detect rotational movement, revolutions, or position of the grasping mechanism 624 to provide corresponding signals to the controller 616 or first control device 626.

In one embodiment, the controller 616 may continue to control the electrical drive mechanism 620 to rotate the grasping mechanism 624 in the second direction until the removal activation is selectively released. In another embodiment, the controller 616 may control the electrical drive mechanism 620 such that the grasping mechanism 624 is automatically rotated a predetermined amount of revolutions in response to the removal activation. The predetermined amount being based at least in part on the revolutions needed to unwind a helical tip of the implantable medical device 612 from an implant location when the implantable medical device 612 is seated at the implant location. As described above for the implant activation, surgical tool 614 may include may include mechanical stops, sensors, or a combination thereof in conjunction with limiting rotational movement to the predetermined amount of revolutions for the removal activation.

In various embodiments of the surgical device 600, the grasping mechanism 624 may include at least one spring resiliently biasing the jaws 630 to the normally closed position. In various embodiments of the surgical device 600, the actuator 632 may include a pneumatic actuator, a linear actuator, a servo actuator, a linear motor, a servo motor, a stepper motor, or any suitable actuator.

In various embodiments of the surgical device 600, the second control device 634 may include a squeeze bulb, a toggle switch, a rotary switch, a slide switch, a single axis joystick, a momentary switch, a foot switch, a peddle switch, or any suitable control device. The squeeze bulb, for example, may have an open position corresponding to a squeeze and a close position corresponding to releasing the squeeze or opening a release valve. The toggle switch, for example, may have an open position and a close position.

In another embodiment, the actuator 632 may include a pneumatic actuator formed by a piston 636 within a cylinder 638. The piston 636 may be adjustably controlled by the second control device 634 between a recessed position and an extended position. In FIG. 6, the piston 636 is shown in the recessed position. The piston 636 may be resiliently biased within the cylinder 638 to the recessed position. The piston 636 may engage the jaws 630 at a predetermined location between the recessed position and the extended position such that when the piston 636 is at the extended position the jaws 630 are at the open position. Additionally, the piston 636 may engage the drive shaft 622 at the recessed position to enable rotational movement of the grasping mechanism 624 when the jaws 630 are in the normally closed position. The piston 636 may disengage from the drive shaft 622 when moved toward the extended position to disable rotational movement of the grasping mechanism 624 when the jaws 630 are not in the normally closed position.

In various embodiments, the actuator 632 may be arranged to rotate with the grasping mechanism 624 when the electrical drive mechanism 620 is activated or to remain stationary with the electrical drive mechanism 620 when the electrical drive mechanism 620 is activated. FIG. 6 shows an arrangement where actuator 632 may rotate with the grasping mechanism 624. In an alternate arrangement (see FIGS. 7-12), the actuator 632 may be disposed proximate to the mechanical interface 618 of the surgical tool 614. In this embodiment, the electrical drive mechanism 224 may include a sleeve that slides over a drive unit. The sleeve may move in concert with the piston to form a linkage or drive train to operate the grasping mechanism 624. In other embodiments, push rods or any suitable linkage or drive train components may be used in place of the sleeve.

In the embodiment being described, the second control device 634 may include a squeeze bulb in fluidic communication with the cylinder 638. The open activation may occur in response to the squeeze bulb being activated one or more times to compress air into the cylinder 638 to move the piston 636 from the recessed position toward the extended position. The second control device 634 in this embodiment may also include a release valve in fluidic communication with the cylinder 638. The close activation may occur in response to the release valve being activated to release compressed air from the cylinder 638 to allow the piston 636 to move toward the recessed position.

In various embodiments of the surgical device 600, the controller 616 and second control device 634 may include various electrical components suitably connected via discrete wiring. In another embodiment, the controller 616 and second control device 634 may include various electrical or electronic components suitably connected via a circuit card assembly.

In various embodiments of the surgical device 600, the controller 616 and second control device 634 may include a power module, a power distribution circuit, a processor, a memory, a storage device, one or more indicator for showing status or sensed operating conditions for the actuator 632, a display device for showing status or sensed operating conditions for the actuator 632, a closed loop controller circuit for feedback control of the actuator 632, a driver circuit providing drive signals to the actuator 632, and a transceiver circuit for communicating with the actuator 632. The power module may include a battery or an adapter to receive standard utility power or another form of electrical power from an external power supply. In this arrangement, the controller 616 may distribute power to any components in the surgical tool 614 needing power via a cable. The cable may also carry drive and control signals for operation of the surgical tool 614.

In yet another embodiment of the surgical device 600, the controller 616 may be wirelessly coupled to the actuator 632. Wireless communication may implement Bluetooth or any suitable wireless communication protocol. In this arrangement, the surgical tool 614 may include a battery or another suitable power source for operation of the actuator 632 and a transceiver circuit for communicating drive and control signals with the controller 616.

In one embodiment, the controller 616 may continue to control the actuator 632 to move the jaws 630 toward the open position until the open activation is selectively released. In another embodiment, the controller 616 may control the actuator 632 such that the jaws 630 are moved to the open position in response to the open activation.

In one embodiment, the controller 616 may continue to control the actuator 632 to move the jaws 630 toward the normally closed position until the close activation is selectively released. In another embodiment, the controller 616 may control the actuator 632 such that the jaws 630 are automatically moved to the close position in response to the close activation. In yet another embodiment, the controller 616 may control the actuator 632 such that the close activation occurs in response to selective release of the open activation.

With reference to FIG. 7, another exemplary embodiment of a surgical tool 714 for manipulation of an implantable medical device 712 may include a mechanical interface 718, an actuator 720, an electrical drive mechanism 724, and a grasping mechanism 730 with two or more jaws 732.

With reference to FIG. 8, a cutaway view of the surgical tool 714 of FIG. 7 is provided. This view shows that the actuator 720 includes a piston 734 within a cylinder 736. This view also shows that the electrical drive mechanism 724 includes a drive unit 738 and sleeve 740 in operative communication with the actuator 720 and grasping mechanism 730. The sleeve 740 slides over the drive unit 738 when the actuator 720 is activated and de-activated to operate the grasping mechanism.

Figure 9:
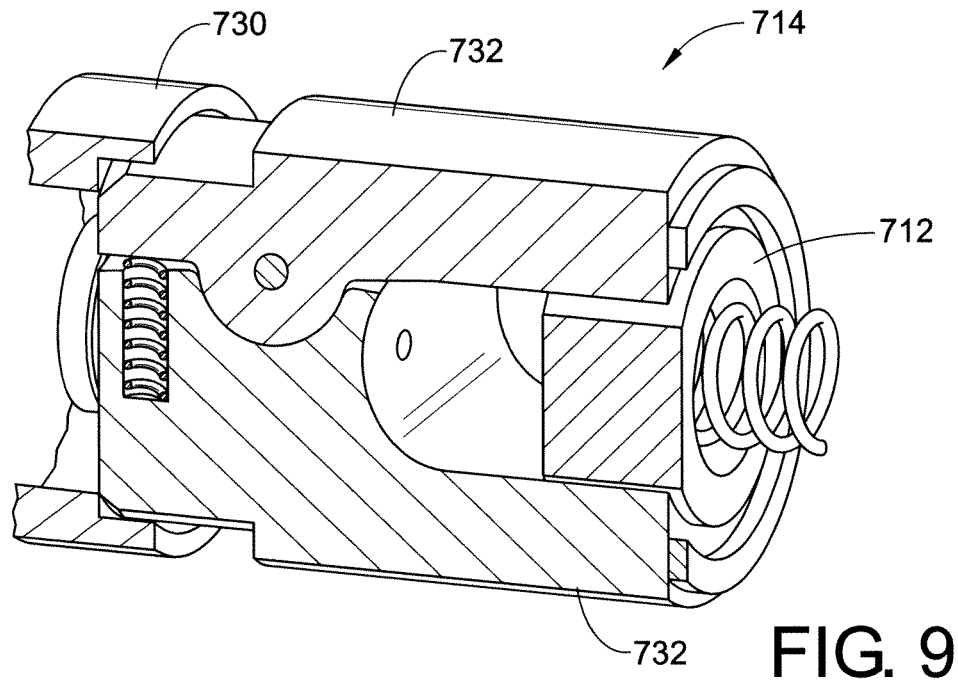
FIG. 9 shows a cross-section view of the surgical tool of FIG. 7.

With reference to FIG. 9, a cross-section view of the surgical tool 714 of FIG. 7 is provided. This view shows the jaws 732 in a normally closed position.

Figure 10:
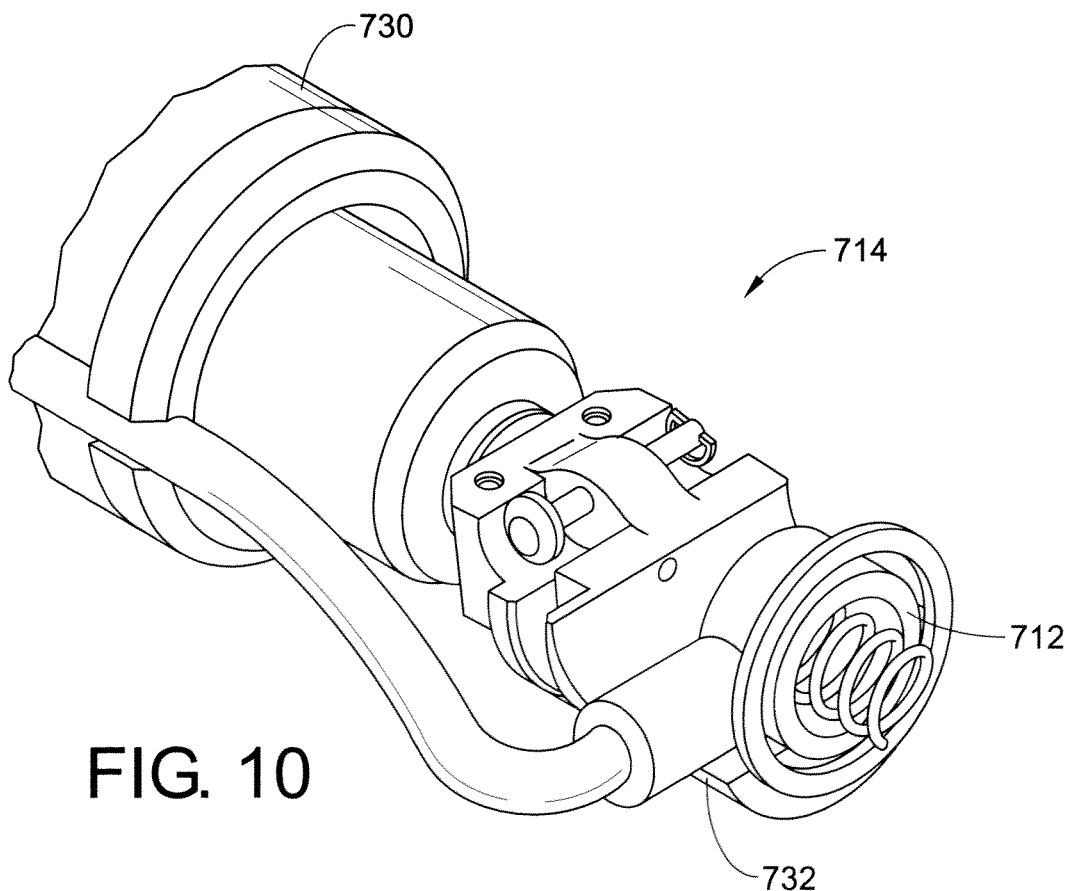
FIG. 10 shows a partially disassembled view of the surgical tool of FIG. 7.

With reference to FIG. 10, a partially disassembled view of the surgical tool 714 of FIG. 7 is provided. An adjustable jaw is removed from the grasping mechanism 730. This view shows a stationary jaw 732 and components that interact with the adjustable jaw.

Figure 11:
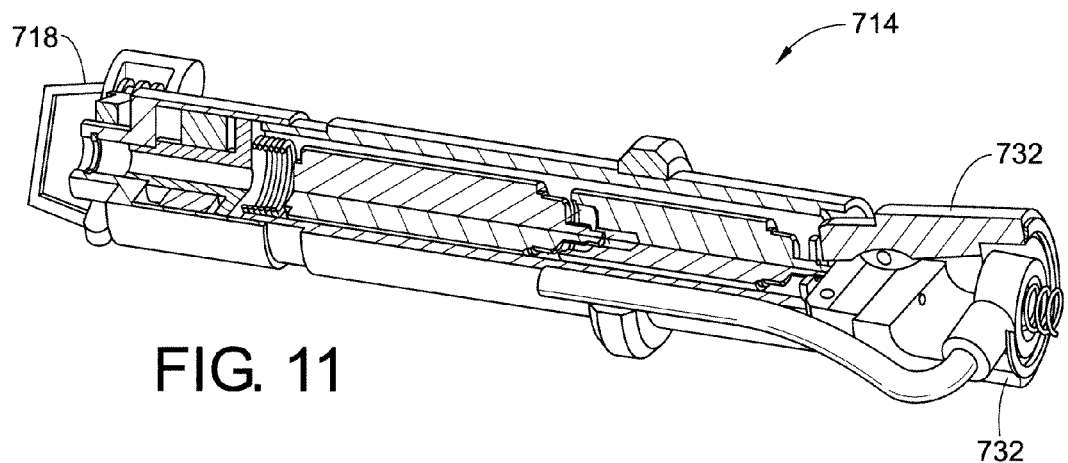
FIG. 11 shows another cutaway view of the surgical tool of FIG. 7.

With reference to FIG. 11, a cutaway view of the surgical tool 714 of FIG. 7 is provided. The view shows the jaws 732 in an open position.

Figure 12:
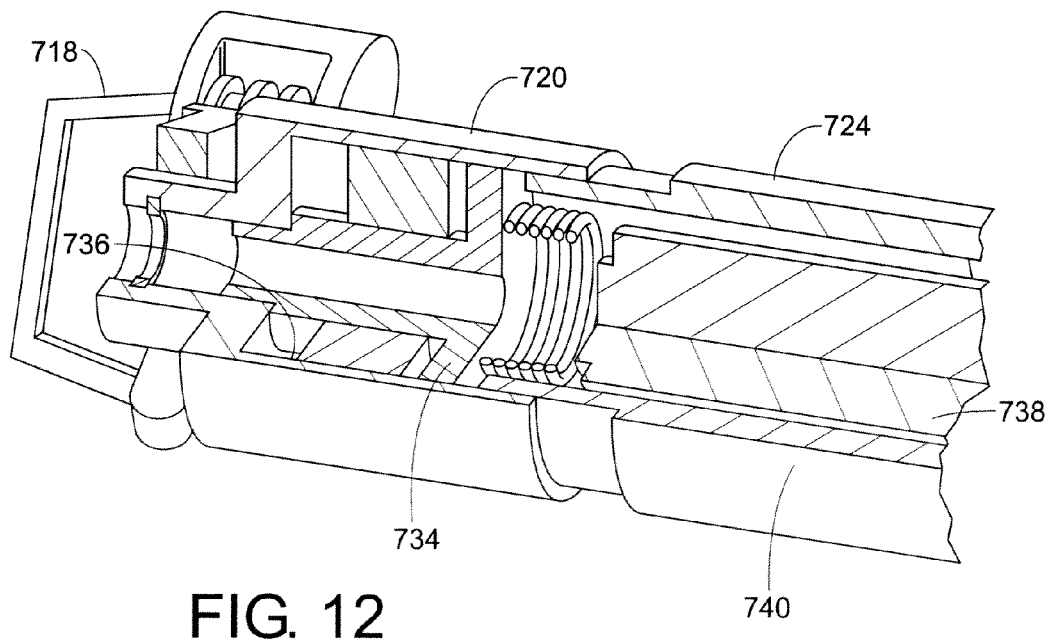
FIG. 12 shows yet another cutaway view of the surgical tool of FIG. 7.

With reference to FIG. 12, another cutaway view of the surgical tool 714 of FIG. 7 is provided. This view shows that the actuator 730 is in an extended position when the jaws 732 of the grasping mechanism 730 are in the open position.

The above description merely provides a disclosure of particular embodiments of the invention and is not intended for the purposes of limiting the same thereto. As such, the invention is not limited to only the above-described embodiments. Rather, it is recognized that one skilled in the art could conceive alternative embodiments that fall within the scope of the invention.

I claim:

1. An apparatus for manipulation of an implantable medical device, comprising:
   a surgical tool, the surgical tool comprising:
      a mechanical interface that enables a surgical instrument to hold and position the surgical tool in conjunction with a surgical procedure;
      an electrical drive mechanism with a drive shaft, the electrical drive mechanism for selectively controlling bidirectional rotation of the drive shaft; and
      a grasping mechanism operationally coupled to the drive shaft such that rotation of the grasping mechanism is driven by the drive shaft, the grasping mechanism for releasably grasping the implantable medical device;
   a controller, comprising:
      a first control device in operative communication with the electrical drive mechanism, wherein an implant activation of the first control device controls the electrical drive mechanism to rotate the grasping mechanism in a first direction and a removal activation of the first control device controls the electrical drive mechanism to rotate the grasping mechanism in a second direction opposite the first direction
   the grasping mechanism comprising:
      a plurality of jaws resiliently biased to a normally closed position for releasably grasping the implantable medical device; and
   the surgical tool, further comprising:
      an actuator operationally coupled to the plurality of laws for selectively controlling the plurality of jaws between the normally closed position and an open position;
      wherein the actuator is configured to engage the drive shaft to enable rotational movement of the grasping mechanism when the jaws are in the closed position and to disengage the drive shaft to disable rotational movement of the grasping mechanism when the jaws are not in the closed position.

2. The apparatus of claim 1, the electrical drive mechanism comprising at least one of a servo motor, a stepper motor, and a gear reduction assembly.

3. The apparatus of claim 1, the first control device comprising at least one of a three-position toggle switch, a three-position rotary switch, a three-position slide switch, a three-position return-to-center switch, a single axis joystick, a set of two momentary switches, a set of two two-position switches, a foot switch, and a peddle switch.

4. The apparatus of claim 1 wherein the controller is wirelessly coupled to at least the electrical drive mechanism.

5. The apparatus of claim 1, the controller further comprising:
   a second control device in operative communication with the actuator, wherein an open activation of the second control device controls the actuator to open the plurality of jaws and a close activation of the second control device controls the actuator to allow the plurality of jaws to move toward the normally closed position.

6. The apparatus of claim 5, the plurality of jaws comprising:
   at least one stationary jaw having a fixed position in relation to the normally closed position and the open position; and
   at least one adjustable jaw resiliently biased to the normally closed position and adjustably controlled by the actuator between the normally closed position and the open position.

7. The apparatus of claim 5, the actuator comprising:
   a pneumatic actuator formed by a piston within a cylinder, the piston adjustably controlled by the second control device between a recessed position and an extended position, wherein the piston is resiliently biased within the cylinder to the recessed position and engages the plurality of jaws at a predetermined location between the recessed position and the extended position such that when the piston is at the extended position the plurality of jaws are at the open position.

8. The apparatus of claim 7, the second control device comprising:
   a squeeze bulb in fluidic communication with the cylinder, wherein the open activation occurs in response to the squeeze bulb being activated one or more times to compress air into the cylinder to move the piston from the recessed position toward the extended position.

9. The apparatus of claim 8, the second control device comprising:
   a release valve in fluidic communication with the cylinder, wherein the close activation occurs in response to the release valve being activated to release compressed air from the cylinder to allow the piston to move toward the recessed position.

10. The apparatus of claim 1 wherein the implantable medical device includes at least one of a therapy delivery tube, a medication delivery tube, a cell delivery tube, a gene delivery tube, and a stem cell delivery tube.

11. A method for manipulation of an implantable medical device, comprising:
   a) providing a surgical device with a surgical tool comprising a mechanical interface, an electrical drive mechanism with a drive shaft, and a grasping mechanism operationally coupled to the drive shaft such that rotation of the grasping mechanism is driven by the drive shaft, the surgical device also including a controller with a first control device in operative communication with the electrical drive mechanism;
   b) holding the surgical tool with a surgical instrument by grasping the mechanical interface;
   c) releasably grasping an implantable medical device with the grasping mechanism;
   d) positioning the surgical tool in conjunction with a surgical procedure using the surgical instrument; and
   e) selectively controlling the electrical drive mechanism to rotate the implantable medical device in a first direction in response to an implant activation of the first control device to wind a helical tip of the implantable medical device into an implant location until the implantable medical device is seated;
   wherein the grasping mechanism comprises a plurality of jaws resiliently biased to a normally closed position, the surgical tool further comprises an actuator operationally coupled to the plurality of jaws, and the controller further comprises a second control device in operative communication with the actuator;
   wherein the actuator is configured to engage the drive shaft to enable rotational movement of the grasping mechanism when the jaws are in the closed position and to disengage the drive shaft to disable rotational movement of the grasping mechanism when the jaws are not in the closed position.

12. The method of claim 11, further comprising:
   f) continuing to control the electrical drive mechanism to rotate the implantable medical device in the first direction until the implant activation of the first control device is selectively released.

13. The method of claim 11 wherein the controller controls the electrical drive mechanism such that the implantable medical device is automatically rotated a predetermined amount of revolutions in response to the implant activation, the predetermined amount being based at least in part on the revolutions needed to wind the helical tip into the implant location until the implantable medical device is seated.

14. The method of claim 11, further comprising:
f) selectively controlling the electrical drive mechanism to rotate the implantable medical device in a second direction opposite the first direction in response to a removal activation of the first control device to unwind the helical tip from the implant location.

15. The method of claim 14, further comprising:
g) continuing to control the electrical drive mechanism to rotate the implantable medical device in the second direction until the removal activation is selectively released.

16. The method of claim 14 wherein the controller controls the electrical drive mechanism such that the implantable medical device is automatically rotated a predetermined amount of revolutions in response to the removal activation, the predetermined amount being based at least in part on the revolutions needed to unwind the helical tip from the implant location when the implantable medical device is seated at the implant location.

17. The method of claim 11, the method further comprising:
f) selectively controlling the actuator to move the plurality of jaws toward an open position in response to an open activation of the second control device;
g) positioning the surgical tool such that the implantable medical device is within range of being grasped by the grasping mechanism; and
h) selectively controlling the actuator to move the plurality of jaws toward the normally closed position in response to a close activation of the second control device to grasp the implantable medical device.

18. The method of claim 11 wherein the implantable medical device includes at least one of a therapy delivery tube, a medication delivery tube, a cell delivery tube, a gene delivery tube, and a stem cell delivery tube.

19. An apparatus for manipulation of an implantable medical device, comprising:
a surgical tool, the surgical tool comprising:
a mechanical interface that enables a surgical instrument to hold and position the surgical tool in conjunction with a surgical procedure;
an electrical drive mechanism with a drive shaft, the electrical drive mechanism for selectively controlling bidirectional rotation of the drive shaft; and
a grasping mechanism operationally coupled to the drive shaft such that rotation of the grasping mechanism is driven by the drive shaft, the grasping mechanism comprising:
a plurality of jaws resiliently biased to a normally closed position for releasably grasping the implantable medical device;
the surgical tool further comprising:
an actuator operationally coupled to the plurality of jaws for selectively controlling the plurality of jaws between the normally closed position and an open position;
wherein the actuator is configured to engage the drive shaft to enable rotational movement of the grasping mechanism when the jaws are in the closed position and to disengage the drive shaft to disable rotational movement of the grasping mechanism when the jaws are not in the closed position; and the apparatus further comprising:
a controller, the controller comprising:
a first control device in operative communication with the electrical drive mechanism, wherein an implant activation of the first control device controls the electrical drive mechanism to rotate the grasping mechanism in a first direction and a removal activation of the first control device controls the electrical drive mechanism to rotate the grasping mechanism in a second direction opposite the first direction; and
a second control device in operative communication with the actuator, wherein an open activation of the second control device controls the actuator to open the plurality of jaws and a close activation of the second control device controls the actuator to allow the plurality of jaws to move toward the normally closed position.

20. The apparatus of claim 19 wherein the controller continues to control the electrical drive mechanism to rotate the grasping mechanism in the first direction until the implant activation is selectively released.

21. The apparatus of claim 19 wherein the controller controls the electrical drive mechanism such that the grasping mechanism is automatically rotated a predetermined amount of revolutions in response to the implant activation, the predetermined amount being based at least in part on the revolutions needed to wind a helical tip of the implantable medical device into an implant location until the implantable medical device is seated.

22. The apparatus of claim 19 wherein the implantable medical device includes at least one of a therapy delivery tube, a medication delivery tube, a cell delivery tube, a gene delivery tube, and a stem cell delivery tube.

* * * * *